United States Patent [19]

Badmin et al.

[11] 4,308,262

[45] Dec. 29, 1981

[54] PYRETHROID PESTICIDAL COMPOSITIONS

[75] Inventors: John S. Badmin; Barry J. Mears, both of Sittingbourne, England

[73] Assignee: Shell Oil Company, Houston, Tex.

[21] Appl. No.: 186,824

[22] Filed: Sep. 12, 1980

[30] Foreign Application Priority Data

Sep. 18, 1979 [GB] United Kingdom ............... 32320/79

[51] Int. Cl.$^3$ ...................... A01N 57/00; A01N 37/34
[52] U.S. Cl. .................................... 424/200; 424/304; 424/305; 424/306; 424/308
[58] Field of Search ................................ 424/200, 304

[56] References Cited

U.S. PATENT DOCUMENTS

| | | | |
|---|---|---|---|
| 3,355,353 | 11/1967 | Jamison | 424/200 |
| 3,835,176 | 9/1974 | Matsuo et al. | 260/465 D |
| 3,996,244 | 12/1976 | Fujimoto et al. | 260/332.2 A |
| 4,024,163 | 5/1977 | Elliott et al. | 260/347.4 |
| 4,171,355 | 10/1979 | Stubbs et al. | 424/174 |

*Primary Examiner*—Allen J. Robinson

[57] ABSTRACT

New pesticidal compositions comprising (a) O,O-diethyl S-(2-chloro-1-phthalimidoethyl)phosphorodithioate and (b) certain pyrethroids are particularly effective against aphids.

2 Claims, No Drawings

PYRETHROID PESTICIDAL COMPOSITIONS

BACKGROUND OF THE INVENTION

1. Field of the Invention

The present invention relates to pesticidal compositions comprising a specific organophosphorus compound and certain pyrethroids and to the use of such compositions for control of pests.

2. Description of the Prior Art

O,O-Diethyl S-(2-chloro-1-phthalimidoethyl)phosphorodithioate, commonly known as dialifos or dialifor is described as a non-systemic insecticide and acaricide in U.S. Pat. No. 3,355,353. On the other hand, natural and synthetic pyrethroids, such as disclosed in U.S. Pat. Nos. 3,835,176, 3,996,244 and 4,024,163, have been of considerable interest because of their quick knockdown activity, low persistence as toxic residues and their low mammalian toxicity. While such compounds are desirable pesticides, because of their relatively complex chemical structures, they tend to be difficult or expensive to manufacture. For certain uses, as increase in the pesticidal spectrum or effectivensss of either the dialifos or the pyrethroids would be desirable.

SUMMARY OF THE INVENTION

It has now been discovered that mixtures of dialifos and certain pyrethroid insecticides exhibit surprising synergistic activity against aphids such as Aphis fabae, the black bean aphid.

The present invention provides a pesticidal composition comprising (a) O,O-diethyl S-(2-chloro-1-phthalimidoethyl)phosphorodithioate, i.e., the compound of the formula I

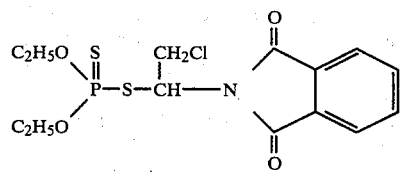

commonly referred to as "dialifos" or "dialifor", and (b) a pyrethroid insecticide having the general formula

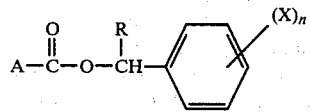

wherein A is an optionally-substituted aralkyl, alkyl, cycloalkyl or arylaminoalkyl group, R is hydrogen, cyano or ethynyl, X is alkyl, alkenyl, aralkyl or aryloxy and n is 1 to 5.

An alkyl, cycloalkyl or alkenyl group represented by A or X preferably contains up to 6 carbon atoms, and an aralkyl, arylaminoalkyl or aryloxy group represented by A or X preferably contains up to 12 carbon atoms.

It should be understood that the compound of the general formula II may be present in the form of any one of its optical or geometric, for example, cis-trans, isomers, or in the form of a mixture of isomers, for example, a racemate. A mixture of two or more compounds according to the general formula II may be present. The compound of formula I may also be present in the form of a pesticidally active optical isomer or a mixture of isomers, for example, the racemate.

When A represents an optionally-substituted cycloalkyl group, it preferably represents a cyclopropyl group of the general formula:

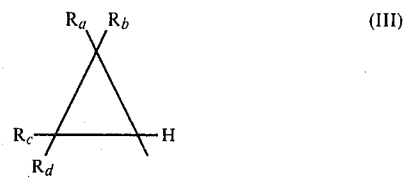

wherein $R_a$ and $R_b$ both represent an alkyl group having from 1 to 6 carbon atoms, especially a methyl group, or a halogen atom, especially a chlorine, bromine or fluorine atom; or $R_a$ and $R_b$ together represent an alkylene group having from 2 to 6, especially 3, carbon atoms; or $R_a$ represents a hydrogen atom and $R_b$ represents an alkenyl group having from 2 to 6 carbon atoms, especially an isobutenyl group, a haloalkenyl group having from 2 to 6 carbon atoms and from 1 to 3 chlorine and/or bromine atoms, especially a monochlorovinyl, monobromovinyl, dichlorovinyl or dibromovinyl group or a haloalkyl group having from 2 to 6 carbon atoms and from 2 to 5 chlorine and/or bromine atoms, especially a tetrachloroethyl, tetrabromoethyl or dibromodichloroethyl group; or $R_a$ and $R_b$ together with the interjacent carbon atom represent an unsaturated carbocyclic ring system of up to 12 carbon atoms, especially an indenylidene group; $R_c$ and $R_d$ both represent an alkyl group having 1 to 6 carbon atoms, especially a methyl group; or $R_c$ and $R_d$ together represent an alkylene group having from 2 to 6, especially 3, carbon atoms. Preferably, $R_a$ and $R_b$ together represent an alkylene group containing 3 carbon atoms, or $R_a$ represents a hydrogen atom and $R_b$ represents an isobutenyl group, a monochlorovinyl, monobromovinyl, dichlorovinyl or dibromovinyl group or a tetrachloroethyl, tetrabromoethyl or dibromodichloroethyl group; or $R_a$ and $R_b$ together with the interjacent carbon atom represent an indenylidene group; and $R_c$ and $R_d$ both represent methyl groups or $R_c$ and $R_d$ together represent an alkylene group containing 3 carbon atoms.

When A in the general formula II represents a optionally-substituted aralkyl group, it preferably represents a substituted benzyl group of the general formula:

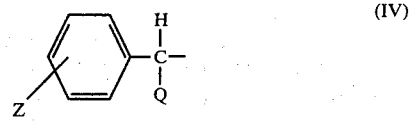

wherein Z represents a halogen, preferably chlorine, atom, or an alkoxy group of 1 to 4 carbon atoms optionally substituted by one or more halogen atoms, for example, a methoxy or difluoromethoxy group, and Q represents an alkyl group of 1 to 6 carbon atoms, especially a branched-chain group, for example, an isopropyl group. Preferably, the group Z is in the 4-position on the benzene ring.

When A represents an optionally-substituted arylaminoalkyl group, it preferably represents a substituted anilinomethyl group of the general formula:

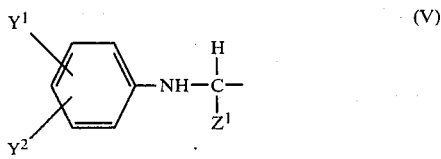

(V)

wherein $Y^1$ and $Y^2$ each independently represents a halogen, preferably chlorine, atom, or an alkyl or haloalkyl group of 1 to 4 carbon atoms, for example, a trifluoromethyl group, and $Q^1$ represents an alkyl group of 1 to 6 carbon atoms, especially a branched-chain group, for example, an isopropyl group. Preferably, $Y^1$ is a chlorine atom in the 2-position on the benzene ring and $Y^2$ is a trifuloromethyl group in the 4-position on the benzene ring.

Preferably, n represents 1 and X represents a phenoxy or a benzyl group, especially a 3-phenoxy or 3-benzyl group.

The most preferred pyrethroid insecticides for use in the pesticidal composition according to the invention have the general formula I wherein A is alpha-isopropyl-4-chlorobenzyl, 2,2,3,3-tetramethylcyclopropyl, 2-(2,2-dichlorovinyl)-3,3-dimethylcyclopropyl, or 2-(2,2-dibromovinyl)-3,3-dimethylcyclopropyl; R is hydrogen or cyano; and n is 1 and X is 3-phenoxy. Especially preferred are the compounds known as cypermethrin, permethrin, decamethrin and fenvalerate whose formulae are given in the Examples herein.

The weight ratio of the pyrethroid insecticide to dialifos is preferably in the range 5:1 to 1:100, more preferably in the rane 1:1 to 1:50 or 1:1 to 1:25 and especially 1:1 to 1:10.

The mixture of dialifos and the pyrethroid insecticides produces a surprising synergistic effect, for example, with respect to aphids, such as *Aphis fabae*, the black bean aphid. The invention therefore also provides a method of combating pests at a locus which comprises applying to that locus a pesticidal composition according to the invention.

The pesticidal composition according to the invention preferably also comprises a carrier, especially at least two carriers, at least one of which is a surface-active agent.

The invention also provides a process for preparing a pesticidal composition which comprises bringing a compound of formula I and a pyrethroid insecticide of formula II into association with at least one carrier therefor.

A carrier in a composition according to the invention is any material with which the active ingredient is formulated to facilitate application to the locus to be treated, which may, for example, be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used.

Suitable solid carriers include natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements, for example, carbon and sulfur; natural and synthetic resins, for example, coumarone resins, polyvinyl chloride, and styrene polymers and copolymers; solid polychlorophenols; bitumen; waxes, for example, beeswax, paraffin wax, and chlorinated mineral waxes; and solid fertilizers, for example, super-phosphates.

Suitable liquid carriers include water; alcohols, for example, isopropanol and glycols; ketones, for example, acetone, methyl ethyl ketone, methyl isobutyl ketone and cyclohexanone; ethers; aromatic or araliphatic hydrocarbons, for example, benzene, toluene and xylene; petroleum fractions, for example, kerosine and light mineral oils; chlorinated hydrocarbons, for example, carbon tetrachloride, perchloroethylene and trichloroethane. Mixtures of different liquids are often suitable.

Pesticidal compositions are often formulated and transported in a concentrated form which is subsequently diluted by the user before application. The presence of small amounts of a carrier which is a surface-active agent facilitates this process of dilution.

A surface-active agent may be an emulsifying agent, a dispersing agent or a wetting agent; it may be non-ionic or ionic. Examples of suitable surface-active agents include the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may, for example, be formulated as wettable powders, dusts, granules, solutions, emulsifiable concentrates, emulsions, suspension concentrates and aerosols. Wettable powders usually contain 25, 50 and 75%w of active ingredient and usually contain, in addition to solid inert carrier, 3-10%w of a dispersing agent and, where necessary, 0-10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing 0.5-10%w of active ingredient. Granules are usually prepared to have a size between 10 and 100 BS mesh (1.676-0.152 mm), and may be manufactured by agglomeration or impregnation techniques. Generally, granules will contain 0.5-25%w active ingredient and 0-10%w of additives such as stabilizers, slow-release modifiers and binding agents. Emulsifiable concentrates usually contain, in addition to a solvent and, when necessary, co-solvent, 10-50% w/v active ingredient, 2-20% w/v emulsifiers and 0-20% w/v of other additives such as stabilizers, penetrants and corrosion inhibitors. Suspension concentrates are usually compounded so as to obtain a stable, non-sedimenting, flowable product and usually contain 10–75%w active ingredient, 0.5–15%w of dispersing agents, 0.1–10%w of suspending agents such as protective colloids and thixotropic agents, 0–10%w of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The compositions of the invention may also contain other ingredients, for example, other compounds possessing pesticidal, herbicidal or fungicidal properties or attractants, for example, pheromones or food ingredients, for use in baits and trap formulations.

The following examples illustrate the invention.

EXAMPLES 1 to 4

Activity of pyrethroid/dialifos mixtures against *Aphis fabae* (black bean aphid)

The coefficients of co-toxicity of cypermethrin, permethrin, decamethrin and fenvalerate with dialifos were assessed by the following method.

Test solutions or suspensions were made up in water containing 0.4% by weight active ingredient, 20% by weight acetone and 0.05% by weight Triton X-100 (Trade Mark). These solutions or suspensions were subsequently diluted to produce compositions containing various concentrations of active ingredient.

Pairs of leaves were removed from broad-bean plants and placed ventral side uppermost on filter paper inside petri dishes. The leaves were sprayed with the test solution using a logarithmic spraying machine and a dosage equivalent to 400 liters/hectare, and allowed to dry for ½–1 hour. Each leaf pair was infested with 10 aphids. Temperature was held constant at 23° C.±2° C., and humidity and light fluctuated. The number of dead and moribund insects was counted after 24 hours. From the results, the $LC_{50}$ (the lethal dosage in percentage by weight required to kill 50% of the test insects) was calculated.

Toxicty indices were then calculated using the following equation:

$$\text{Toxicity Index (T.I.)} = \frac{LC_{50} \text{ of ethyl parathion (standard)}}{LC_{50} \text{ of test compound}}$$

The joint action of the two active components of a mixture was analyzed by the method of Yun-Pei Sun and E. R. Johnson, *J. Econ. Entomol.*, 53, No. 5, pp 887–892 (1960).

Thus, the joint action of two pesticides were analyzed by determining the actual toxicity indices of the components and of mixtures of the compounds by reference to dosage-mortality curves. The theoretical toxicity of the mixture is equal to the sum of toxicity indices calculated from the percentage of each component multiplied by its respective toxicity index. Therefore, the joint toxicity or Co-toxicity coefficient of a mixture $$= \frac{\text{Actual toxicity index of a mixture}}{\text{Theoretical toxicity index of a mixture}} \times 100$$

A coefficient of a mixture near 100 indicates probability of similar action by the two pesticides; independent action usually should give a coefficient less than 100, while a coefficient significantly above 100 strongly indicates synergism.

Cypermethrin, the pyrethroid insecticide used in Example 1, has the formula:

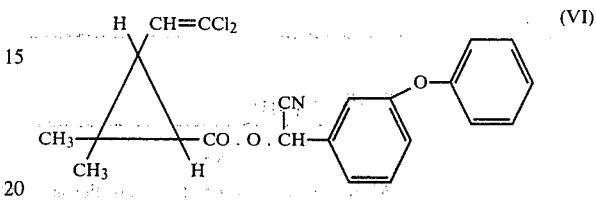
(VI)

Fenvalerate, the pyethroid insecticide used in Example 2, has the formula:

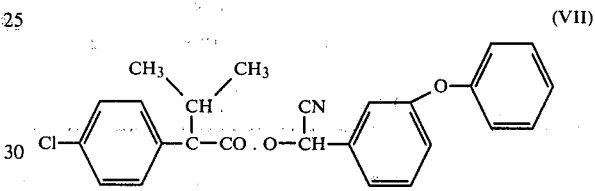
(VII)

Permethrin, the pyrethroid insecticide used in Example 3, has the formula

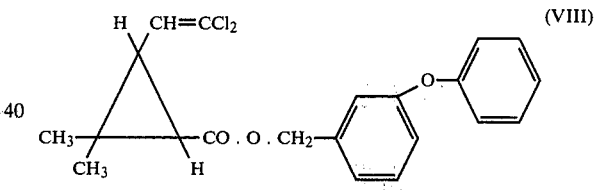
(VIII)

Decamethrin, the pyrethroid insecticide used in Example 4, has the formula

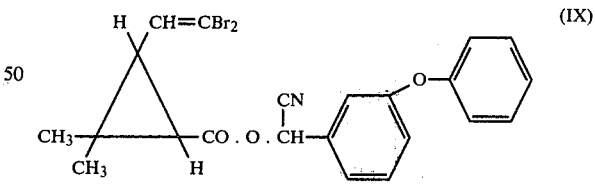
(IX)

(1R-cis-S isomer)

The results of the Examples are given in Tables I to IV following:

TABLE I

| Compound or Compound Mixture | Weight Ratio of Mixture | $LC_{50}$ % wt of Solution | Coefficient of Co-toxicity |
|---|---|---|---|
| cympermethrin | | 0.00086 | |
| dialifos | | 0.043 | |
| cypermethrin/ dialifos | 1:25 | 0.010 | 143 |
| ethyl parathion | | 0.014 | |

TABLE I

| Compound or Compound Mixture | Weight Ratio of Mixture | LC$_{50}$ % wt of Solution | Coefficient of Co-toxicity |
| --- | --- | --- | --- |
| fenvalerate | | 0.0020 | |
| dialifos | | 0.043 | |
| fenvalerate/ dialifos | 1:10 | 0.0075 | 202 |
| ethyl parathion | | 0.014 | |

TABLE III

| Compound or Compound Mixture | Weight Ratio of Mixture | LC$_{50}$ % wt of Solution | Coefficient of Co-toxicity |
| --- | --- | --- | --- |
| permethrin | | 0.0023 | |
| dialifos | | 0.043 | |
| permethrin/ dialifos | 1:10 | 0.013 | 121 |
| ethyl parathion | | 0.0034 | |

TABLE IV

| Compound or Compound Mixture | Weight Ratio of Mixture | LC$_{50}$ % wt of Solution | Coefficient of Co-toxicity |
| --- | --- | --- | --- |
| decamethrin | | 0.00016 | |
| dialifos | | 0.043 | |
| decamethrin/ dialifos | 1:100 | 0.0093 | 123 |
| ethyl parathion | | 0.0034 | |

The coefficients of co-toxicity in Tables I to IV indicate synergism in the mixtures tested.

We claim:

1. An aphicidal composition comprising
(a) O,O-diethyl S-(2-chloro-1-phthalimidoethyl)phosphorodithioate, and
(b) a pyrethroid insecticide of formula II

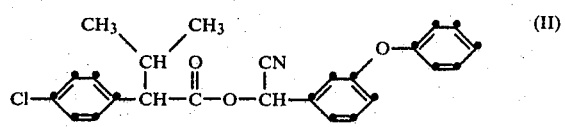

in a ratio of (a) to (b) of 10 to 1.

2. A method of combating aphid pests at a locus which comprises applying to the locus an aphicidally-effective amount of a composition according to claim 1.

* * * * *